United States Patent
Hidaka et al.

(10) Patent No.: US 11,427,546 B2
(45) Date of Patent: Aug. 30, 2022

(54) FORM OF ISOQUINOLINE SULFONAMIDE

(71) Applicant: D. WESTERN THERAPEUTICS INSTITUTE, INC., Nagoya (JP)

(72) Inventors: Hiroyoshi Hidaka, Nagoya (JP); Kengo Sumi, Nagoya (JP); Takashi Izuhara, Nagoya (JP)

(73) Assignee: D. WESTERN THERAPEUTICS INSTITUTE, INC., Nagoya (JP)

( * ) Notice: Subject to any disclaimer, the term of this patent is extended or adjusted under 35 U.S.C. 154(b) by 0 days.

(21) Appl. No.: 17/296,439

(22) PCT Filed: Dec. 16, 2019

(86) PCT No.: PCT/JP2019/049099
§ 371 (c)(1),
(2) Date: May 24, 2021

(87) PCT Pub. No.: WO2020/129876
PCT Pub. Date: Jun. 25, 2020

(65) Prior Publication Data
US 2022/0017469 A1   Jan. 20, 2022

(30) Foreign Application Priority Data

Dec. 17, 2018 (JP) .............................. JP2018-235213

(51) Int. Cl.
*C07D 217/22* (2006.01)

(52) U.S. Cl.
CPC ........ *C07D 217/22* (2013.01); *C07B 2200/13* (2013.01)

(58) Field of Classification Search
CPC .......................... C07D 217/22; C07B 2200/13
See application file for complete search history.

(56) References Cited

U.S. PATENT DOCUMENTS

| 5,340,811 A | 8/1994 | Kajihara et al. |
| 5,942,505 A | 8/1999 | Kawakubo et al. |
| 2008/0021018 A1 | 1/2008 | Ohshima et al. |
| 2009/0156823 A1 | 6/2009 | Kida et al. |
| 2013/0274269 A1* | 10/2013 | Hidaka .................. A61P 27/02 546/139 |

FOREIGN PATENT DOCUMENTS

| JP | 2899953 B2 | 6/1999 |
| JP | 5819705 B2 | 11/2015 |
| WO | WO 2006/057397 A1 | 6/2006 |
| WO | WO 2009/004792 A1 | 1/2009 |
| WO | WO 2012/086727 A1 | 6/2012 |

OTHER PUBLICATIONS

International Search Report dated Feb. 10, 2020 in PCT/JP2019/049099 filed Dec. 16, 2019, 3 pages.
Takata Noriyuki, "API form screening and selection in drug discovery stage", Pharm Stage, vol. 6, No. 10, 2007, pp. 20-25, 8 total pages.
Wermuth, C. G. ed. Nagase, Hiroshi supervising tr., The Practice of Medicinal Chemistry, last Vol. Technomics, Inc., 1999, chapter 34, sections 1, 2, 5, 20 total pages.
Hirayama, Noriaki ed., Organic Compound Crystal production handbook: Principles and Knowhow. Maruzen Co., Ltd., 2008, sections 4.1, 4.5, pp. 58-84, 16 total pages.
Ogata, Akira, How to Conduct Chemical Experiments, first vol. Nankodo Co., Ltd., 1963, p. 366-399.
Indian Office Action dated Nov. 24, 2021 in Indian Patent Application No. 202117026399, 7 pages.
Supplementary European Search Report dated Jun. 15, 2022, in European Patent Application No. 1989054.1.
R. Hilfiker, et al., "Relevance of Solid-state Properties for Pharmaceutical Products", In: Hilfiker R.: Polymorphism in the Pharmaceutical Industry:, Wiley-VCH, Verlag Gmbh, ISBN: 978-3-527-31146-0, pp. 1-19 (Jan. 2006).
M. Caira, "Crystalline Polymorphism of Organic Compounds", Topics in Current Chemistry. vol. 198, pp. 163-208 (Jan. 1998).

* cited by examiner

*Primary Examiner* — Timothy R Rozof
(74) *Attorney, Agent, or Firm* — Oblon, McClelland, Maier & Neustadt, L.L.P.

(57) ABSTRACT

A stable crystal of a salt of N—[(R)-1-{(S)-2-hydroxy-2-phenylpropylamino}propan-2-yl]isoquinoline-6-sulfonamide may have desirable properties for a pharmaceutical drug substance, and more specifically N—[(R)-1-{(S)-2-hydroxy-2-phenylpropylamino}propan-2-yl]isoquinoline-6-sulfonamide dihydrochloride anhydride. A crystal of the anhydride may have characteristic peaks at 2θ angles of 6.8±0.1°, 10.0±0.1°, 12.7±0.1°, 14.6±0.1°, 14.8±0.1°, 16.2±0.1°, 17.4±0.1°, 17.8±0.1°, 19.5±0.1°, 20.0±0.1°, 21.6±0.1°, 24.7±0.1°, 25.5±0.1°, 25.8±0.1°, 29.8±0.1°, 39.5±0.1°, and/or 44.9±0.1° in powder X-ray diffraction spectrum.

6 Claims, 5 Drawing Sheets

FIG. 7

| Compound | Parameter | Standing time point | | Percent increase | Day 7 photographic appearance |
|---|---|---|---|---|---|
| | | Day 0 | Day 7 | | |
| Monohydrochloride (1) | Weight | 100 mg | 111 mg | 11% | |
| | Appearance | White solid | Light-yellow paste | | |
| Dihydrochloride (2) | Weight | 102 mg | 102 mg | 0% | |
| | Appearance | White crystal | White crystal | | |

FIG. 8

| Compound | Parameter | Standing time point | | | Percent increase | Photographic appearance after standing |
|---|---|---|---|---|---|---|
| | | Day 0 | | Day 3 | | |
| | | 0 h | 1 h | | | |
| Compound (3) | Weight | 100 mg | 115 mg | - | 15% | |
| | Appearance | White solid | Light-yellow paste | - | | |
| Compound (4) | Weight | 100 mg | 117 mg | - | 17% | |
| | Appearance | White solid | Light-yellow paste | - | | |
| Dihydrochloride (2) | Weight | 100 mg | 100 mg | 100 mg | 0% | |
| | Appearance | White crystal | White crystal | White crystal | | |

FIG. 9

| Compound | Parameter | Storage time point | | |
|---|---|---|---|---|
| | | Day 0 | Day 7 | Day 14 |
| Monohydrochloride (1) | Appearance | White solid | White foamy matter | - |
| | Purity (%) | 98.4 | 98.5 | - |
| Dihydrochloride (2) | Appearance | White crystal | White crystal | White crystal |
| | Purity (%) | 99.7 | 99.7 | 99.7 |

FIG. 10

| Parameter | Compound in aqueous solution | |
|---|---|---|
| | Monohydrochloride (1) | Dihydrochloride (2) |
| Appearance | Translucent | Colorless and clear |
| Precipitate | Observed | Not observed |

FORM OF ISOQUINOLINE SULFONAMIDE

CROSS-REFERENCE TO RELATED APPLICATIONS

The present application is the national stage of international application PCT/JP2019/049099, filed on Dec. 16, 2019, and claims the benefit of the filing date of Japanese Appl. No. 2018-235213, filed on Dec. 17, 2018.

FIELD OF THE INVENTION

The present invention relates to a new form of an isoquinoline sulfonamide compound that is useful as a pharmaceutical.

BACKGROUND OF THE INVENTION

N—[(R)-1-{(S)-2-hydroxy-2-phenylpropylamino}propan-2-yl]isoquinoline-6-sulfonamide monohydrochloride is a compound represented by the following formula (1), and it is described in Patent Document 1 as being useful as a glaucoma therapeutic and hypotensive agent. Traditionally, compound (1), a monohydrochloride, has been known as the only salt of N—[(R)-1-{(S)-2-hydroxy-2-phenylpropylamino}propan-2-yl]isoquinoline-6-sulfonamide.

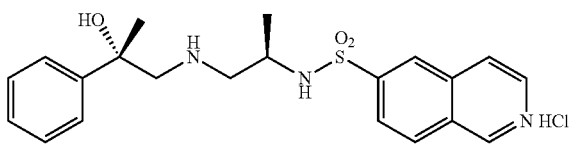

(1)

When placed in the ambient atmosphere and exposed to air for a given length of time, a solid powder of compound (1) gradually loses its powder nature, degrading to a highly viscous paste. This is because compound (1) is highly hygroscopic. This nature not only poses a great burden on pharmaceutical manufacturers and others, but also calls for special attention from the viewpoint of quality control during storage, which presents a problem to be solved in view of the handleability of compound (1) for a pharmaceutical drug substance.

While compound (1) is classified as what is called an isoquinoline sulfonamide compound, the following compounds have so far been known as stable crystals of drugs of this kind: 1-(5-isoquinolinesulfonyl)homopiperazine hydrochloride hemihydrate (Patent Document 2), (S)-(−)-1-(4-fluoroisoquinolin-5-yl)sulfonyl-2-methyl-1,4-homopiperazine hydrochloride dihydrate (Patent Document 3), (S)-(−)-1-(4-fluoroisoquinolin-5-yl)sulfonyl-2-methyl-1,4-homopiperazine hydrochloride anhydride (Patent Document 4), and (S)-1-(4-chloro-5-isoquinolinesulfonyl)-3-(methylamino)pyrrolidine monohydrochloride (Patent Document 5). As is evident from these examples, a stable crystal of isoquinoline sulfonamide compound has been acquired in the form of an anhydride or hydrate of its monohydrochloride; however, although compound (1) is a monohydrochloride, any desired stable crystal has been obtained neither as an anhydride nor as a hydrate.

CITATION LIST

Patent Document

[Patent Document 1] International Patent Publication 2012/086727
[Patent Document 2] Japanese Patent No. 2899953
[Patent Document 3] International Patent Publication 2006/057397
[Patent Document 4] Japanese Patent No. 5819705
[Patent Document 5] International Patent Publication 2009/004792

SUMMARY OF THE INVENTION

Technical Problem

Accordingly, the present invention is intended to acquire a stable crystal of a salt of N—[(R)-1-{(S)-2-hydroxy-2-phenylpropylamino}propan-2-yl]isoquinoline-6-sulfonamide having desirable properties for a pharmaceutical drug substance.

Solution to Problem

The present inventors conducted extensive investigations to obtain a stable salt of N—[(R)-1-{(S)-2-hydroxy-2-phenylpropylamino}propan-2-yl]isoquinoline-6-sulfonamide, unexpectedly finding that compound (2), which is represented by the following formula, exhibits extremely high stability. Specifically, compound (2) is a dihydrochloride anhydride, and was found to stabilize in the form of a salt distinct from that of any conventional isoquinoline sulfonamide compound. Compound (2) was found not to exhibit atmospheric hygroscopicity as with compound (1), and to be stable to heat. Furthermore, in terms of water solubility, compound (2) was more favorable than compound (1).

In general, a pharmaceutical drug substance is desirably in the form of a crystal. Powder X-ray diffraction analysis of compounds (1) and (2) for crystallinity showed that compound (1) was amorphous, whereas compound (2) exhibited crystallinity.

These findings showed that compound (2) had physicochemical properties that are evidently more suitable for a pharmaceutical drug substance than those of compound (1).

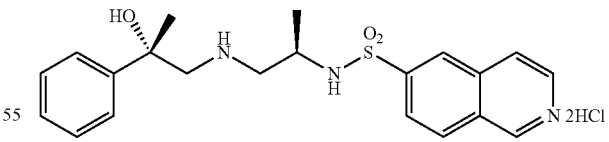

(2)

Hence, the present invention provides the following entities described in terms [1] to [8]:

[1] N—[(R)-1-{(S)-2-hydroxy-2-phenylpropylamino}propan-2-yl]isoquinoline-6-sulfonamide dihydrochloride anhydride.

[2] A crystal of N—[(R)-1-{(S)-2-hydroxy-2-phenylpropylamino}propan-2-yl]isoquinoline-6-sulfonamide dihydrochloride anhydride having characteristic peaks at 2θ angles of 6.8±0.1°, 10.0±0.1°, 12.7±0.1°, 14.6±0.1°, 14.8±0.1°, 16.2±0.1°, 17.4±0.1°, 17.8±0.1°, 19.5±0.1°, 20.0±0.1°, 21.6±0.1°, 24.7±0.1°, 25.5±0.1°, 25.8±0.1°, 29.8±0.1°, 39.5±0.1°, and 44.9±0.1° in powder X-ray diffraction spectrum.

[3] A crystal of N—[(R)-1-{(S)-2-hydroxy-2-phenylpropylamino}propan-2-yl]isoquinoline-6-sulfonamide dihydrochloride anhydride having characteristic peaks at about 703±5, 1143±5, 1165±5, 1174±5, 1325±5, 1655±5, 2558±5, 2634±5, 2691±5, 3122±5, 3235±5, and 3396±5 cm$^{-1}$ in infrared absorption spectrum.

[4] A crystal of N—[(R)-1-{(S)-2-hydroxy-2-phenylpropylamino}propan-2-yl]isoquinoline-6-sulfonamide dihydrochloride anhydride having an endothermic peak at about 237° C.±5° C. in differential scanning calorimetric analysis.

[5] A crystal of N—[(R)-1-{(S)-2-hydroxy-2-phenylpropylamino}propan-2-yl]isoquinoline-6-sulfonamide dihydrochloride anhydride having a water content of from 0% to 0.16% in a water content determination by the Karl Fischer method.

[6] A manufacturing method for the crystal of N—[(R)-1-{(S)-2-hydroxy-2-phenylpropylamino}propan-2-yl]isoquinoline-6-sulfonamide dihydrochloride anhydride described in any one of terms [2] to [5], comprising adding not less than 2 equivalents of hydrochloric acid to N—[(R)-1-{(S)-2-hydroxy-2-phenylpropylamino}propan-2-yl]isoquinoline-6-sulfonamide, dissolving the resulting solid in ethanol and water, and precipitating the crystal using a non-ethanol polar solvent.

[7] A pharmaceutical composition comprising the N—[(R)-1-{(S)-2-hydroxy-2-phenylpropylamino}propan-2-yl]isoquinoline-6-sulfonamide dihydrochloride anhydride described in any one of terms [1] to [5] and a pharmaceutically acceptable carrier.

[8] Use of the N—[(R)-1-{(S)-2-hydroxy-2-phenylpropylamino}propan-2-yl]isoquinoline-6-sulfonamide dihydrochloride anhydride described in any one of terms [1] to [5] for pharmaceutical manufacture.

Effect of the Invention

A crystal of the N—[(R)-1-{(S)-2-hydroxy-2-phenylpropylamino}propan-2-yl]isoquinoline-6-sulfonamide dihydrochloride anhydride of the present invention is less hygroscopic, more stable to heat, and more soluble in water than compound (1). Therefore, the dihydrochloride anhydride (2) of the present invention is a useful salt form having desirable properties for a pharmaceutical drug substance. Specifically, when a salt of N—[(R)-1-{(S)-2-hydroxy-2-phenylpropylamino}propan-2-yl]isoquinoline-6-sulfonamide is manufactured or used as a pharmaceutical drug substance, the use of compound (2), which is a stable dihydrochloride anhydride, makes it easier to handle the salt from the viewpoint of not only workability, but also quality control. When compound (2) is used as a solution formulation, no special operations in the formulation step nor additives, etc. to improve the solubility are required, and there are only a few concerns about precipitation under refrigeration, etc., because of its good solubility in water.

BRIEF DESCRIPTION OF THE DRAWINGS

FIG. 7 shows the moisture absorption stability of compound (2) and compound (1).

FIG. 8 shows the moisture absorption stability of compound (2), compound (3), and compound (4).

FIG. 9 shows the heat stability of compound (2) and compound (1).

FIG. 10 shows the water solubility of compound (2) and compound (1).

DETAILED DESCRIPTION OF THE INVENTION

Figure 1:
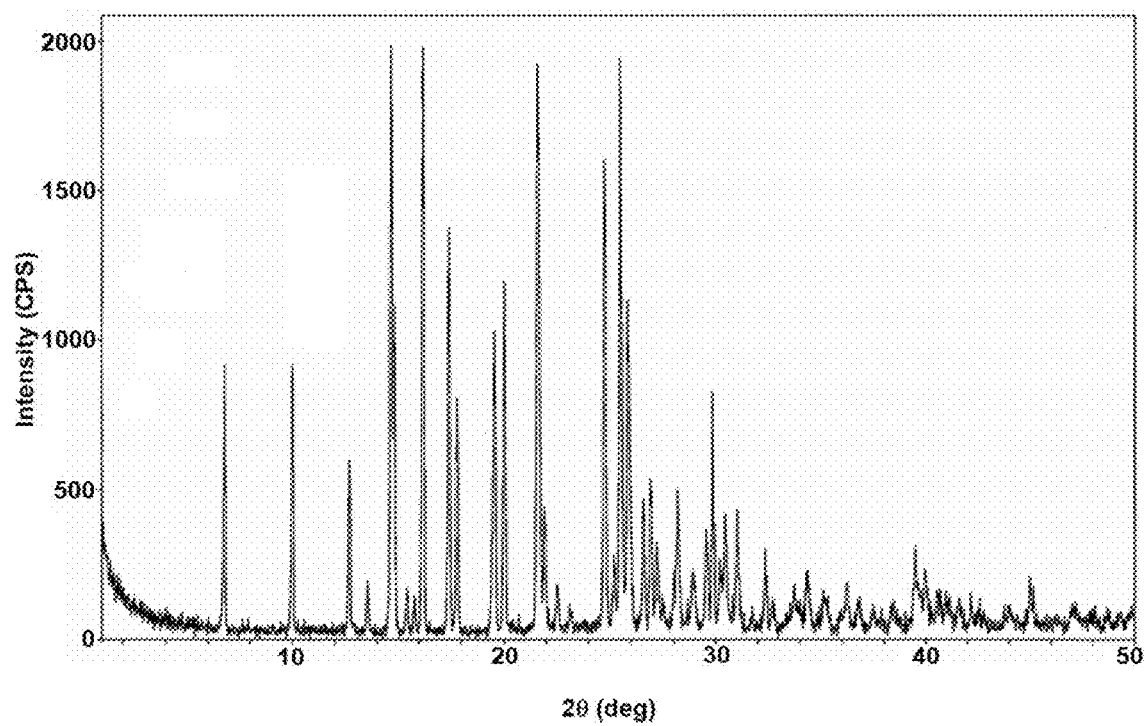
FIG. 1 shows a powder X-ray diffraction spectrum of compound (2).

The N—[(R)-1-{(S)-2-hydroxy-2-phenylpropylamino}propan-2-yl]isoquinoline-6-sulfonamide dihydrochloride anhydride of the present invention can be manufactured using the following method:

First, the free form N—[(R)-1-{(S)-2-hydroxy-2-phenylpropylamino}propan-2-yl]isoquinoline-6-sulfonamide can be manufactured using the method described in Patent Document 1. When 2 equivalents or more of hydrochloric acid is added to the thus-obtained free form dissolved in an organic solvent, a crystal of dihydrochloride anhydride is obtained. By dissolving the resulting crystal in ethanol and water, and precipitating the solute using a non-ethanol polar solvent such as acetonitrile, 1,4-dioxane, acetone, or isopropyl alcohol, a highly pure crystal can be manufactured.

In more detail, the free form becomes a crystal of dihydrochloride anhydride when 2 equivalents or more of hydrochloric acid is added after the free form is dissolved in an organic solvent such as dichloromethane, 1,4-dioxane, or ethanol. The amount of organic solvent used here may be an amount that allows the free form to dissolve therein. The amount of hydrochloric acid added may be an amount of 2 equivalents or more, and there is no need to add it in large excess.

The resulting crystal of dihydrochloride is dissolved in 30° C.-80° C. ethanol, water is added at the same temperature, and the mixture is stirred to completely dissolve the crystal. The amount of ethanol used here is preferably from 6 to 30 mL per gram of the crystal of dihydrochloride. The amount of water used is preferably from 1 to 3 mL per gram of the crystal of dihydrochloride.

Subsequently, by adding a non-ethanol polar solvent such as acetonitrile, 1,4-dioxane, acetone, or isopropyl alcohol, and cooling the mixture to 0° C.-30° C., a highly pure crystal of the compound (2) of the present invention can be obtained. The amount of non-ethanol polar solvent used here is preferably from 18 to 90 mL per gram of the crystal of dihydrochloride. A highly pure crystal as mentioned herein refers to one having an HPLC purity of 99% or higher.

The resulting compound (2) is a crystal, having characteristic peaks at 2θ angles of 6.8±0.1°, 10.0±0.1°, 12.7±0.1°, 14.6±0.1°, 14.8±0.1°, 16.2±0.1°, 17.4±0.1°, 17.8±0.1°, 19.5±0.1°, 20.0±0.1°, 21.6±0.1°, 24.7±0.1°, 25.5±0.1°, 25.8±0.1°, 29.8±0.1°, 39.5±0.1°, and 44.9±0.1° in powder X-ray diffraction spectrum. Here, powder X-ray diffraction can be measured by exposure to a copper Kα ray.

In addition, compound (2) has characteristic peaks at about 703±5, 1143±5, 1165±5, 1174±5, 1325±5, 1655±5, 2558±5, 2634±5, 2691±5, 3122±5, 3235±5, and 3396±5 cm$^{-1}$ in infrared absorption spectrum.

Compound (2) has an endothermic peak at about 237° C.±5° C. in differential scanning calorimetric analysis. In addition, compound (2) has a water content of from 0% to 0.16% in a water content determination by the Karl Fischer method.

As shown in FIG. 7 or FIG. 8, the compound (2) of the present invention did not at all exhibit any weight change due to water absorption in the ambient atmosphere or during storage at 50° C./70% RH. The compound (1) described in Patent Document 1 or compounds (3) and (4), on the other hand, were found to exhibit a weight gain due to water absorption and marked property change under the respective conditions. Furthermore, as shown in FIG. 9, the compound (2) of the present invention was stable at 70° C., whereas compound (1) was unstable with an evident change in appearance. These findings showed that the compound (2) of the present invention was less hygroscopic and more stable to heat than compound (1). When a 5% aqueous solution of each of compound (1) and the compound (2) of the present invention was prepared, and their transparencies were compared, the aqueous solution of compound (2) was colorless and clear, whereas the aqueous solution of compound (1) was translucent and had not dissolved completely. Hence, the results suggested that the compound (2) of the present invention has a higher water solubility (FIG. 10).

The compound (2) of the present invention is useful as an active ingredient for glaucoma therapeutics and hypotensive agents.

The compound (2) of the present invention can be administered both orally and parenterally. Dosage forms that can be used include tablets, capsules, granules, powders, injections, and eye lotions, which may be used in combination with commonly used techniques.

For oral formulations such as tablets, capsules, granules, and powders, the following, for example, may be prepared in combination with the present invention compound as required: excipients such as lactose, mannitol, starch, crystalline cellulose, light silicic anhydride, calcium carbonate, and calcium hydrogen phosphate; lubricants such as stearic acid, magnesium stearate, and talc; binders such as starch, hydroxypropylcellulose, hydroxypropylmethylcelllulose, and polyvinylpyrrolidone; disintegrants such as carboxymethylcelllulose, low-substitutional hydroxypropylmethylcelllulose, and calcium citrate; coating agents such as hydroxypropylmethylcelllulose, macrogol, and silicone resin; stabilizers such as ethyl para-oxybenzoate and benzyl alcohol; taste/odor correctives such as sweeteners, souring agents, and flavors; and other additives.

For parenteral preparations such as injections and eye lotions, the following, for example, may be prepared in combination with the present invention compound (2) as required: isotonizing agents such as glycerol, propylene glycol, sodium chloride, potassium chloride, sorbitol, and mannitol; buffering agents such as phosphoric acid, phosphates, citric acid, glacial acetic acid, s-aminocaproic acid, and trometamol; pH regulators such as hydrochloric acid, citric acid, phosphoric acid, glacial acetic acid, sodium hydroxide, potassium hydroxide, sodium carbonate, and sodium hydrogen carbonate; solubilizers or dispersing agents such as polysorbate 80, polyoxyethylene hardened castor oil 60, macrogol 4000, purified soybean lecithin, and polyoxyethylene (160) polyoxypropylene (30) glycol; cellulose polymers such as hydroxypropylmethylcelllulose and hydroxypropylcellulose; thickening agents such as polyvinyl alcohol and polyvinylpyrrolidone; stabilizers such as edetic acid and sodium edetate; general-purpose preservatives or antiseptics such as sorbic acid, potassium sorbate, benzalkonium chloride, benzetonium chloride, methyl para-oxybenzoate, propyl para-oxybenzoate, and chlorobutanol; and analgesics such as chlorobutanol, benzyl alcohol, and lidocaine.

In the case of an injection or eye lotion, it is desirable that the pH be set at from 4.0 to 8.0, and that osmotic pressure ratio be set at about 1.0.

A dose of the compound (2) of the present invention can be optionally chosen according to symptoms, age, dosage form, and other factors. In the form of an oral formulation, for example, the compound (2) of the present invention can be administered usually at a daily dose of from 0.01 to 1000 mg, preferably from 1 to 100 mg, once or in several divided doses.

In the form of an eye lotion, the compound (2) of the present invention can be administered usually at a concentration of from 0.0001% to 10% (w/v), preferably from 0.01% to 5% (w/v), once or in several divided doses.

In the case of intravenous administration, the daily dose rages from 0.1 to 100 mg per person, preferably from 1 to 30 mg per person. In the case of oral administration, the daily dose rages from 1 to 1000 mg per person, preferably from 10 to 30 mg per person. In some cases, a lower dose is sufficient; in other cases, a higher dose may be required. The compound (2) of the present invention may be administered in two to three divided doses per day.

EXAMPLES

The present invention is hereinafter described specifically by means of the following Examples and Test Examples, which, however, are not to be construed as limiting the present invention.

Synthesis of Crystal of N—[(R)-1-{(S)-2-hydroxy-2-phenylpropylamino}propan-2-yl]isoquinoline-6-sulfonamide dihydrochloride anhydride Example 1

N—[(R)-1-{(S)-2-hydroxy-2-phenylpropylamino}propan-2-yl]isoquinoline-6-sulfonamide manufactured using the method described in Patent Document 1 (0.374 g) was dissolved in ethanol (10 mL), 2M hydrochloric acid diethyl ether solution (2 mL) was added at room temperature, and the mixture was stirred for 2 hours. The precipitated solid was filtered, and the resulting filtrate was dried under reduced pressure to obtain a crystal (0.378 g).

Ethanol (200 mL) was added to the thus-obtained crystal (33.4 g), and water (40 mL) was added with stirring at 80° C. to completely dissolve the crystal. Acetonitrile (600 mL) was added, and the mixture was stirred at room temperature for 2 hours. The precipitated solid was filtered, and the resulting filtrate was dried under reduced pressure to obtain a highly pure white crystal (25.0 g, HPLC purity 99.7%). $^1$H NMR (D$_2$O, δ ppm) 0.83 (3H, d), 1.73 (3H, s), 2.98 (1H, dd), 3.19 (1H, dd), 3.44 (1H, d), 3.64 (1H, d), 3.79-3.80 (1H, m), 7.45 (1H, dd), 7.53 (2H, dd), 7.59 (2H, dd), 8.25 (1H, dd), 8.51 (1H, d), 8.62 (1H, d), 8.69 (1H, d), 8.73 (1H, s), 9.74 (1H, s). MS m/z 400 [M+H]$^+$.

Example 2

The crystal of N—[(R)-1-{(S)-2-hydroxy-2-phenylpropylamino}propan-2-yl]isoquinoline-6-sulfonamide dihydrochloride anhydride obtained in Example 1 (250 mg) was subjected to the same operations as Example 1 except that 1,4-dioxane was used in place of acetonitrile, to obtain a highly pure white crystal (216 mg). The $^1$H NMR data were the same as those of the crystal obtained in Example 1.

Example 3

The crystal of N—[(R)-1-{(S)-2-hydroxy-2-phenylpropylamino}propan-2-yl]isoquinoline-6-sulfonamide dihydrochloride anhydride obtained in Example 1 (250 mg) was subjected to the same operations as Example 1 except that acetone was used in place of acetonitrile, to obtain a highly pure white crystal (200 mg). The 1H NMR data were the same as those of the crystal obtained in Example 1.

Example 4

The crystal of N—[(R)-1-{(S)-2-hydroxy-2-phenylpropylamino}propan-2-yl]isoquinoline-6-sulfonamide dihydrochloride anhydride obtained in Example 1 (250 mg) was subjected to the same operations as Example 1 except that isopropyl alcohol was used in place of acetonitrile, to obtain a highly pure white crystal (120 mg). The $^1$H NMR data were the same as those of the crystal obtained in Example 1.

Synthesis of reference compounds is described below. Although Patent Document 1 does not describe in detail how to prepare the monohydrochloride and dihydrochloride, it is possible to control the number of added hydrochloric acid molecules by adding 1 equivalent of hydrochloric acid or 2 equivalents or more of hydrochloric acid to the free compound.

Reference Example 1

Synthesis of N—[(R)-1-{(S)-2-hydroxy-2-phenylpropylamino}propan-2-yl]isoquinoline-6-sulfonamide monohydrochloride (1)

N—[(R)-1-{(S)-2-hydroxy-2-phenylpropylamino}propan-2-yl]isoquinoline-6-sulfonamide manufactured using the method described in Patent Document 1 (1.95 g) was dissolved in dichloromethane (5 mL) and diethyl ether (20 mL), 1M hydrochloric acid diethyl ether solution (4.7 mL) was added at room temperature, and the mixture was stirred for 2 hours. Thereafter, the precipitated solid was filtered, and the resulting filtrate was dried under reduced pressure to obtain the desired product as a white solid (1.85 g, HPLC purity 98.4%). The $^1$H NMR data agreed with the data shown in Patent Document 1.

Reference Example 2

Synthesis of (R)—N-{1-(phenetylamino)propan-2-yl}isoquinoline-6-sulfonamide dihydrochloride (3)

The title compound was obtained as a white solid using the method described in Patent Document 1. The 1H NMR data agreed with the data shown in Patent Document 1.

Reference Example 3

Synthesis of N—[(R)-1-{(R)-2-phenyipropylamino}propan-2-yl]isoquinoline-6-sulfonamide dihydrochloride (4)

The title compound was obtained as a white solid using the method described in Patent Documents 1. The 1H NMR data agreed with the data shown in Patent Document 1.

The thus-obtained highly pure crystal of the compound (2) of the present invention was subjected to elemental analysis, powder X-ray diffraction, infrared absorption spectrometry, differential scanning calorimetric analysis, and moisture content measurement. The results are shown below.

(1) Elemental Analysis

Results of elemental analysis of compound (2) (MICRO CORDER JM10 model from J-SCIENCE LAB Co., Ltd.) are shown below. The numeric values in the parentheses are calculated values from the molecular formula $C_{21}H_{27}C_{12}N_3O_3S$ for the compound (2) of the present invention. C, 53.30% (53.39%); H, 5.78% (5.76%); N, 8.91% (8.89%)

(2) Powder X-Ray Diffraction

Figure 2:
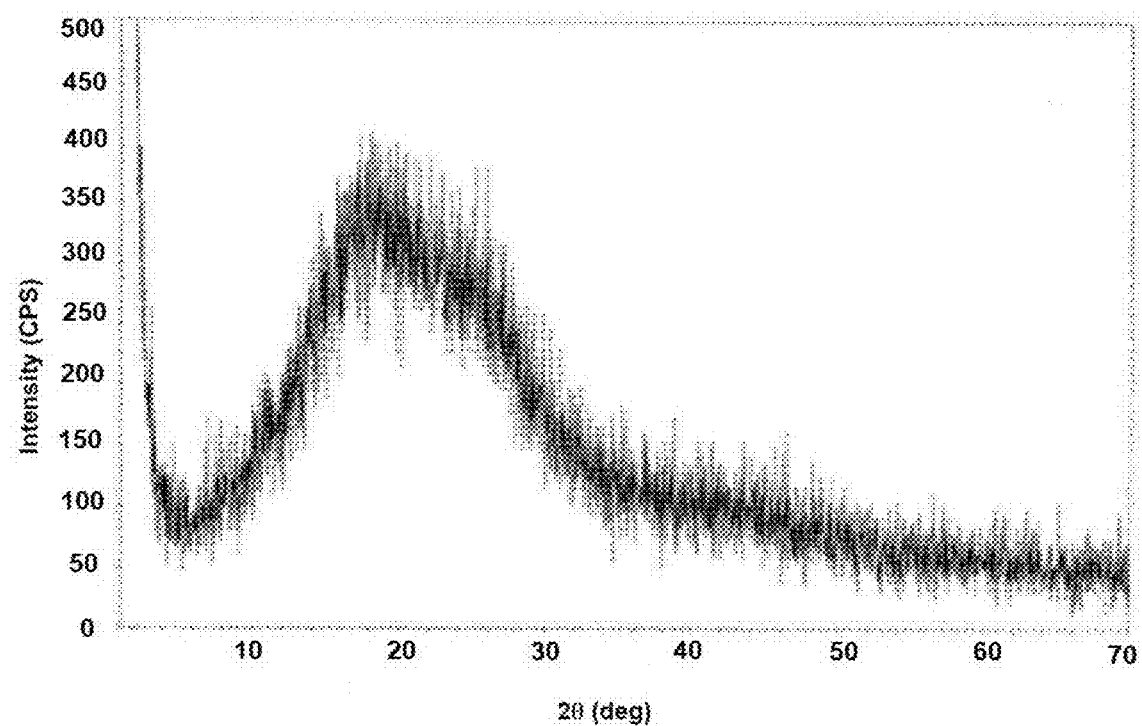
FIG. 2 shows a powder X-ray diffraction spectrum of compound (1).

In powder X-ray diffraction (RINT-TTRIII model wide-angle X-ray diffraction analyzer from Rigaku Corporation), a crystal of the dihydrochloride anhydride (2) of the present invention exhibited the pattern shown in FIG. 1 with characteristic peaks at diffraction angles (2θ) of 6.80°, 10.0°, 12.7°, 14.6°, 14.8°, 16.2°, 17.4°, 17.8°, 19.50, 20.00, 21.60, 24.70, 25.50, 25.80, 29.80, 39.50, and 44.9°. Shown for reference in FIG. 2 is a powder X-ray diffraction spectrum of compound (1). As is evident from FIG. 2, compound (1), unlike the compound (2) of the present invention, was amorphous.

(3) Infrared Absorption Spectra

Figures 3, 4:
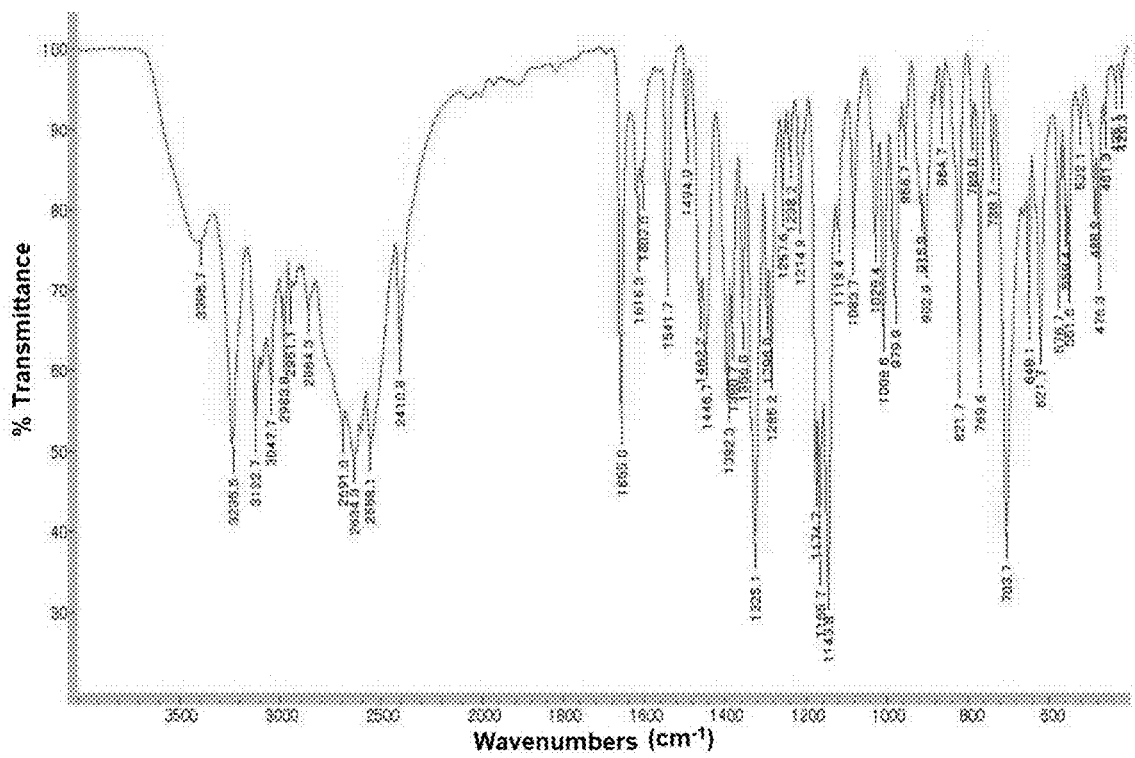
FIG. 3 shows an infrared absorption spectrum of compound (2).
FIG. 4 shows an infrared absorption spectrum of compound (1).

When determined using an infrared spectrophotometer (FTS7000e from Agilent Technologies, Inc.), the infrared absorption spectrum of a crystal of the compound (2) of the present invention exhibited the pattern shown in FIG. 3 with characteristic peaks at about 703, 1143, 1165, 1174, 1325, 1655, 2558, 2634, 2691, 3122, 3235, and 3396 cm$^{-1}$. Shown for reference in FIG. 4 is an infrared absorption spectrum of compound (1). As is evident from FIG. 4, compound (1) exhibited absorption peaks distinct from those of the compound (2) of the present invention.

(4) Differential Scanning Calorimetric Analysis

Figure 5:
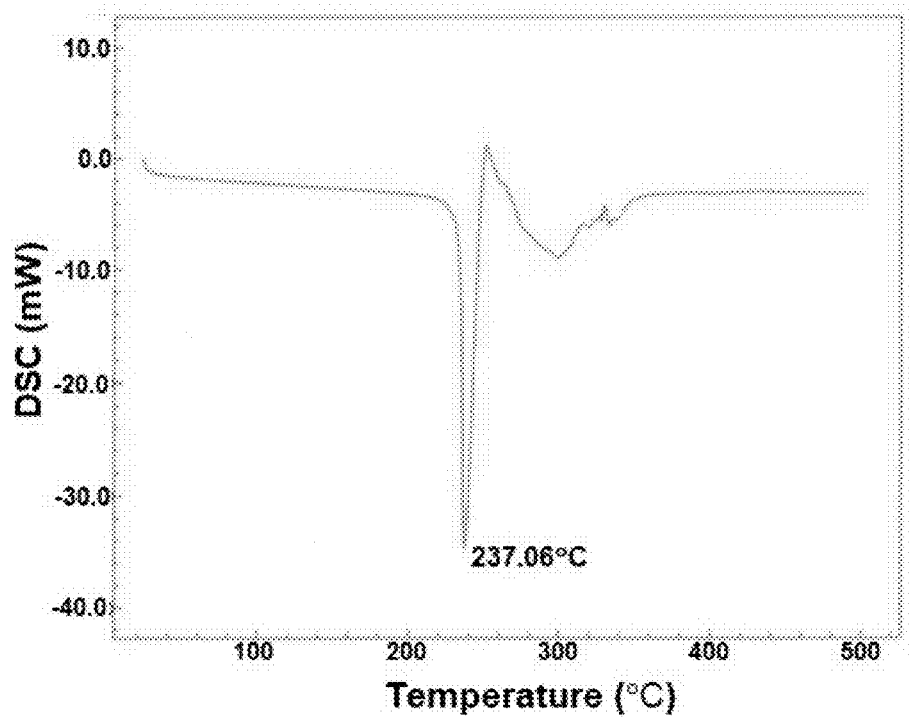
FIG. 5 shows a differential scanning calorimetric analysis result of compound (2).
Figure 6:
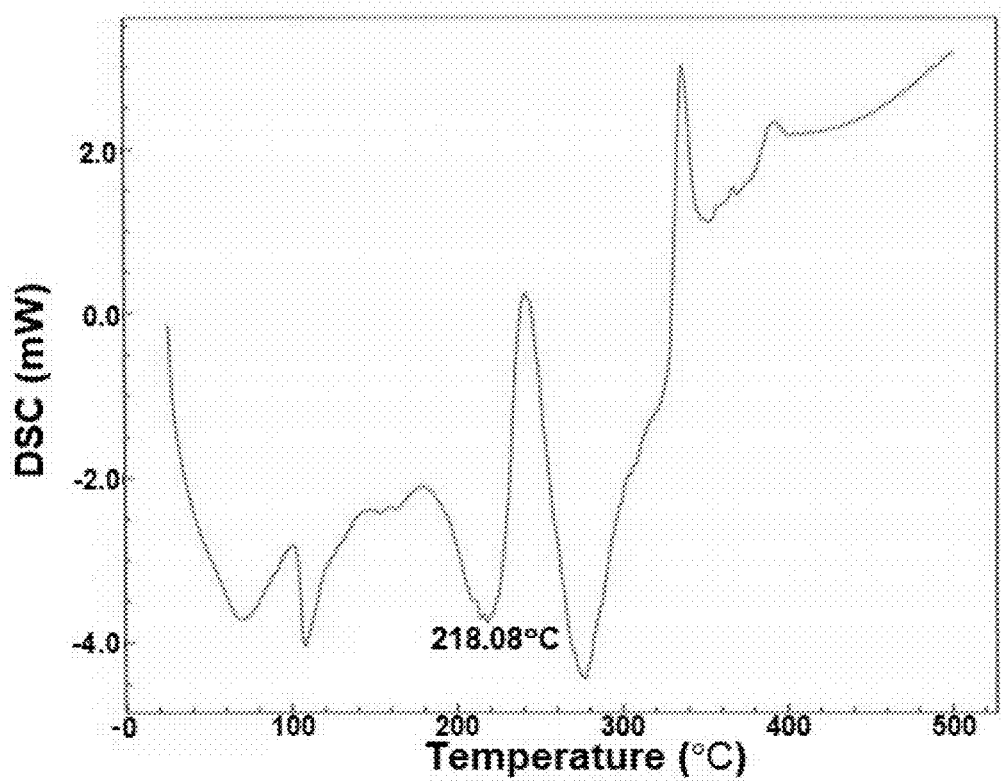
FIG. 6 shows a differential scanning calorimetric analysis result of compound (1).

In differential scanning calorimetric analysis (DSC-50 differential scanning calorimeter from Shimadzu Corporation), the endothermic peak of the crystal of the compound (2) of the present invention was at 237° C., as shown in FIG. 5. Shown for reference in FIG. 6 are results of differential scanning calorimetric analysis of compound (1). As is evident from FIG. 6, compound (1) exhibited an endothermic peak distinct from that of the compound (2) of the present invention.

(2) Water Content

As determined using the Karl Fischer method (MKC-610 Karl Fischer moisture meter from Kyoto Electronics Manufacturing Co., Ltd.), the water content of the crystal of the compound (2) of the present invention was 0.16%.

Test Example 1

Moisture Absorption Stability Comparative Test in the Ambient Atmosphere

About 100 mg of each of the compound (1) obtained in Reference Example 1 and the compound (2) of the present invention obtained in an Example was weighed out in a plastic container and allowed to stand in the ambient atmosphere (25° C.-28° C./67%-83% RH), while minimizing the influence of wind pressure, foreign matter entry, and the like from above and all directions, for 7 days. On Day 0 and Day 7, samples were weighed and examined for appearance.

The results are shown in FIG. 7. Compound (1) exhibited a percent increase in weight of 11% on Day 7. In addition, an evident moisture absorption phenomenon was noted in appearance, strongly suggesting the weight gain to be due to water absorption. On the other hand, the compound (2) of the present invention exhibited no weight gain or appearance change even on Day 7.

These findings showed that the compound (2) of the present invention was less hygroscopic than compound (1).

Test Example 2

Moisture Absorption Stability Comparative Test at 50° C./70% RH

A 100-mg weight of each of the crystals of compounds (3) and (4) obtained in Reference Examples 2 and 3, respectively, and the compound (2) of the present invention obtained in an Example was weighed out in a plastic container and allowed to stand under 50° C./70% RH conditions in a thermo-hygrostat chamber (IH400 from Yamato Scientific Co., Ltd.).

The results are shown in FIG. 8. Compounds (3) and (4) exhibited a marked appearance change due to moisture absorption after 1 hour of standing, and their weights increased by 15% and 17%, respectively. Therefore, the testing was prematurely discontinued. On the other hand, the crystal of the compound (2) of the present invention exhibited no appearance change nor weight gain. Likewise, after 3 days of standing, no change was observed, nor was there any change in the powder X-ray diffraction peak pattern.

These findings showed that compounds (3) and (4) exhibited evidently higher hygroscopicity, although they are dihydrochlorides of molecules structurally analogous to the compound (2) of the present invention.

Test Example 3

Heat Stability Comparative Test

About 20 mg of each of the compound (1) of Reference Example 1 and the crystal of the compound (2) of the present invention obtained in an Example was weighed out in a glass vial and stored in a thermostat chamber kept at 70° C. in an airtight state (NA-100N Incubator from NISSIN) for 14 days. On Day 0, Day 7, and Day 14, compound (1) and the compound (2) of the present invention were examined for appearance and purity (HPLC).

The results are shown in FIG. 9. The solid of compound (1) adhered firmly to the bottom of the glass vial on Day 7, and its appearance changed to a foamy matter with volume expansion, showing a marked property degradation. Therefore, the testing was prematurely discontinued. On the other hand, the crystal of the compound (2) of the present invention was stable, with no change in appearance nor decomposition, even on Day 14. Nor was there any change in the powder X-ray diffraction peak pattern.

Test Example 4

Water Solubility Comparative Test

About 100 mg of each of the compound (1) of Reference Example 1 and the crystal of the compound (2) of the present invention was weighed out in a glass vial, 2 mL of purified water was added, and the mixture was vigorously shaken in an airtight state. After being allowed to stand until the liquid surface fluctuation ceased, the aqueous solution was examined for transparency by visual observation at room temperature.

The results are shown in FIG. 10. The aqueous solution of compound (1) was translucent. The aqueous solution of the crystal of the compound (2) of the present invention, on the other hand, was extremely clear, showing complete dissolution. In addition, 1 day later, a precipitate was found on the bottom of the vial of the aqueous solution of compound (1), whereas no precipitate was found from the compound (2) of the present invention.

INDUSTRIAL APPLICABILITY

The N—[(R)-1-{(S)-2-hydroxy-2-phenylpropylamino}propan-2-yl]isoquinoline-6-sulfonamide dihydrochloride anhydride (2) according to the present invention is a new crystal having not only low hygroscopicity, but also high stability to heat and good water solubility, thus possessing extremely desirable properties for a pharmaceutical drug substance.

The invention claimed is:

1. N—[(R)-1-{(S)-2-hydroxy-2-phenylpropylamino}propan-2-yl]isoquinoline-6-sulfonamide dihydrochloride anhydride, in the form of a crystal having characteristic peaks at 2θ angles of 6.8±0.1°, 10.0±0.1°, 12.7±0.1°, 14.6±0.1°, 14.8±0.1°, 16.2±0.1°, 17.4±0.1°, 17.8±0.1°, 19.5±0.1°, 20.0±0.1°, 21.6±0.1°, 24.7±0.1°, 25.5±0.1°, 25.8±0.1°, 29.8±0.1°, 39.5±0.1°, and 44.9±0.1° in powder X-ray diffraction spectrum.

2. The anhydride of claim 1, in the form of a crystal having characteristic peaks at about 703±5, 1143±5, 1165±5, 1174±5, 1325±5, 1655±5, 2558±5, 2634±5, 2691±5, 3122±5, 3235±5, and 3396±5 cm$^{-1}$ in infrared absorption spectrum.

3. The anhydride of claim 1, in the form of a crystal having an endothermic peak at about 237° C.±5° C. in differential scanning calorimetric analysis.

4. The anhydride of claim 1, in the form of a crystal having a water content in a range of from 0% to 0.16% in a water content determination by the Karl Fischer method.

5. A manufacturing method for the crystal of N—[(R)-1-{(S)-2-hydroxy-2-phenylpropylamino}propan-2-yl]isoquinoline-6-sulfonamide dihydrochloride anhydride of claim 1, comprising:
   adding not less than 2 equivalents of hydrochloric acid to N—[(R)-1-{(S)-2-hydroxy-2-phenylpropylamino}propan-2-yl]isoquinoline-6-sulfonamide,
   dissolving the resulting solid in ethanol and water, and precipitating the crystal using a non-ethanol polar solvent.

6. A pharmaceutical composition comprising:
   the N—[(R)-1-{(S)-2-hydroxy-2-phenylpropylamino}propan-2-yl]isoquinoline-6-sulfonamide dihydrochloride anhydride of claim 1; and
   a pharmaceutically acceptable carrier.

* * * * *